(12) United States Patent
Bonati et al.

(10) Patent No.: US 6,596,064 B2
(45) Date of Patent: Jul. 22, 2003

(54) BIOCIDAL-ANTIFOULING AGENTS WITH LOW ECOTOXICITY INDEX

(75) Inventors: Stefano Bonati, Milan (IT); Francesco Monteleone, Cassina de' Pecchi (IT)

(73) Assignee: Luigi Stoppani S.p.A., Milan (IT)

( * ) Notice: Subject to any disclaimer, the term of this patent is extended or adjusted under 35 U.S.C. 154(b) by 0 days.

(21) Appl. No.: 10/025,740

(22) Filed: Dec. 26, 2001

(65) Prior Publication Data

US 2002/0117079 A1 Aug. 29, 2002

Related U.S. Application Data

(63) Continuation-in-part of application No. 09/684,656, filed on Oct. 10, 2000, now abandoned.

(30) Foreign Application Priority Data

Oct. 15, 1999 (IT) .......................................... MI99A2166

(51) Int. Cl.⁷ ............................. A01N 35/06; C09D 5/14
(52) U.S. Cl. ............................... 106/18.34; 106/15.05; 106/18.33; 514/245; 514/247; 514/676; 514/682
(58) Field of Search ........................... 106/15.05, 18.33, 106/18.34; 514/245, 247, 676, 682

(56) References Cited

U.S. PATENT DOCUMENTS 2,367,302 A   1/1945   Moore et al. ............... 514/682
3,328,169 A   6/1967   Nanninga ................... 514/245

FOREIGN PATENT DOCUMENTS

EP   0 152 852   8/1985
JP   03-131669 *  6/1991

OTHER PUBLICATIONS

Database chemabs 'online! Chemical Abstract Service, Columbus, Ohio, US; Koniya, Kazumi et al: "Antifouling agents containing vitamin K" retrieved from STN Database accession No. 111:210596 XP002161675 abstract & JP 01 031702 A (Ihara Chemical Industry Co., LTD., Japan) Feb. 2, 1989.
Chemical abstracts, vol. 115, No. 22, 1991 Columbus, Ohio, US; abstract No. 234844y, Yokoi, Junji et al.: "Antifouling coatings" XP002161673 abstract & JP 03 131669 A (Nippon Paint) Jun. 5, 1991.
Chemical abstracts, vol. 125, No. 8, 96 Columbus, Ohio, US; abstract No. 89317d, Myamoto, Takashi: "Antifouling coating compositions" XP002161674 abstract & JP 08 104 832 A (Toyo Boseki) Apr. 23, 1996.
Database Chemabs 'Online! Chemical abstracts service, Columbus, Ohio, US; Wu, Guoyao et al: "Microbicidal coatings or sheets containing vitamin K3, for optical instruments" retrieved from STN Database accession No. 113:138576 XP002161676 abstract & CN 1 036 689 A (Hunan Institute of Metering and Test Technics, Peop. Rep. China) Nov. 1, 1989.
Derwent Patent Abstract No. 1966–22586F, abstract of Japanese Patent Specification No. 66–014238 (Jan. 1966).

* cited by examiner

Primary Examiner—Anthony J. Green
(74) Attorney, Agent, or Firm—Guido Modiano; Albert Josif; Daniel O'Byrne

(57) ABSTRACT

A use of tetralin derivatives as biocidal and antifouling agents for preventing and slowing the growth of algae, molds and microorganisms. In particular, the vitamin derivatives are constituted by salts of menadione bisulfite with the heterocyclic bases triazine and piperazine.

7 Claims, No Drawings

BIOCIDAL-ANTIFOULING AGENTS WITH LOW ECOTOXICITY INDEX

This is a Continuation-In-Part Application based on U.S. Ser. No. 09/684,656, filed on Oct. 10, 2000, now abandoned.

BACKGROUND OF THE INVENTION

The present invention relates to biocidal-antifouling agents with low ecotoxicity index.

In particular, the present invention relates to the use of tetralin derivatives effective as biocidal and antifouling agents for preventing and slowing the growth of algae, molds and microorganisms.

Menadione and its derivatives are vitamin derivatives which have an antihemorrhagic activity and have long been used in the medical and veterinary field, as disclosed in U.S. Pat. No. 2,367,302.

In particular, adducts of menadione bisulfite with heterocycles such as triazine, pyrimidine, guanidine have been described in U.S. Pat. No. 3,328,169, while adducts of menadione bisulfite with pyridine derivatives are known from Italian Patent No. 1,097,391.

Up to now, the only indication for use of these menadione bisulfite adducts, salified with heterocyclic bases, has been based on their antihemorrhagic activity. Accordingly, these compounds have been applied in the veterinary field as medicines and as additives for feeds meant for farm animals and fish.

In JP 03-131669, Yokoi et al. provides antifouling coatings containing naphthoquinone and/or p-hydroxyquinone derivatives having a biocidal activity.

In JP 66-014238, a compound for treating skin infections, the formulation comprising menadione (2-methyl-1,4-naphtaquinone, i.e. vitamin $K_3$) and curcumin dissolved in a solvent such as ethanol, is provided.

There was a need in the art for new biocidal agents, having improved antifouling properties with low antifouling toxicity.

Surprisingly, it has now been found that there is another unexpected indication for use of menadione bisulfite adducts salified with heterocyclic bases in a technical field which is entirely different from the one in which menadione derivatives are currently and commonly used.

Specifically, it has now been found surprisingly that these compounds have a great ability to inhibit and slow the deposition and growth of a layer of living organisms such as a layer of vegetation, mold or microorganisms on the surfaces of objects and structures exposed to humidity or immersed in fresh or salt water.

SUMMARY OF THE INVENTION

One of the aims of the present invention is to provide new indications for use for a group of compounds correlated to the menadione bisulfite heterocyclic base salts.

Another object is to provide biocidal and antifouling agents which are highly effective in preventing the adhesion of algae, molds and colonies of microorganisms on surfaces of objects and structures exposed to humidity or immersed in water.

Another object is to provide a class of compounds having a biocidal and/or antifouling activity which have minimal ecotoxicity and polluting activity and can therefore be used in the ecosystem without compromising its balance.

In view of this aim, these objects and others which will become apparent hereinafter, and in accordance with a first aspect of the present invention, use of menadione bisulfite adducts salified with organic bases as biocidal and/or antifouling agent is provided.

Within the scope of the present invention, the said derivatives are selected from the group consisting of menadione triaminotriazine bisulfite (I) (MTB) and menadione (bis) piperazine bisulfite (II) (MBP). The compounds according to the present invention are used as antifouling and biocidal agents having low ecotoxicity and minimal polluting activity with respect to the ecosystem.

The compounds according to the invention are used whenever materials, objects and structures need to be protected from the growth of vegetation or colonies of unwanted microorganisms. In particular, the compounds according to the invention are suitable to prevent and limit the growth of algae and molds on the surfaces of objects that make contact with water or with ambient moisture for prolonged periods of time.

In particular, these objects and structures include watercraft hulls, submerged masonry or metallic structures, floating transport or signaling means, fishing nets, and cooling systems which use seawater.

The materials that can be treated with the compounds according to the invention are materials of various origin, commonly used in the manufacture of items which make contact with fresh water or salt water, such as for example steel, concrete, glass, plastics, rubber, wood, textile fibers, leather, et cetera.

The use according to the present invention advantageously provides for the addition or application of an amount which is effective from an antifouling and/or biocidal standpoint of a compound of the above described type to a material or structure exposed to water or moisture.

The compounds according to the invention are also suitable in the prevention and slowing of mold growth.

For this use, the compounds according to the invention are advantageously added to water-based emulsion paints, to adhesives, cellulose-based glues, fluids for machining and cooling metals, lubricating fluids for spools of thread, systems and raw materials for the processing of paper and for the preservation of tanned hides.

It has also been found surprisingly that MTB and MBP according to the invention have a biocidal activity against the most disparate bacterial strains that form colonies on the above cited objects and structures.

The compounds of the invention are used in amounts which vary according to the type of application and can be easily determined by a person skilled in the field. Suitable concentrations for the use of the invention can vary from a few ppm (0.0001% by weight for use as antifouling in cooling water such as in power stations, steelworks) up to concentrations of 40%, by weight (formulation for antifouling paints). An effective biocidal concentration for menadione and derivatives thereof is advantageously in the range of 0.5% to 10% by weight, preferably of 1 to 5% by weight.

The compounds according to the invention can be applied pure or added to carriers, such as powders, nebulizing agents and dispersants, or can be dissolved or suspended in a liquid, and in this case they are usually accompanied by wetting agents or emulsifiers in order to promote uniform dispersion of the active principle.

In the case of use of MTB and MBP adducts as mold preventers for fluids such as lubricants used in the machining of metals or lubricants for spools of thread, cellulose-based adhesives, for example wallpaper, said adducts can be used in suspension or emulsion, associated with wetting agents or emulsifiers, preferably at concentrations between 3 and 15% by weight.

The compounds according to the invention are furthermore used in the preparation of formulations of antifouling paints preferably in amounts which can vary between 3 and 15% by weight, advantageously in association with base materials.

The base materials for antifouling paints include binding agents such as synthetic and natural resins, homo- and copolymers, synthetic and natural caoutchouc, acrylic polyurethane epoxy resins or preparations of monomers to be polymerized in place to which the antifouling agent is added.

The use of menadione bisulfite derivatives according to the invention allows to considerably limit the problems of pollution and ecotoxicity caused by the use, in marine paints, of antifouling agents which are usually based on heavy metal derivatives.

The compounds according to the invention have proved themselves highly toxic and repellent both against microorganisms which tend to form colonies and against algae and molds.

Differently from commonly used antifouling agents, which are based on heavy metals, the derivatives according to the invention, by having a common non-toxic vitamin matrix, are not a source of pollution for the environment.

This advantage is more evident when the compounds according to the invention are used in the cooling of industrial plants located in coastal regions, since in this case enormous amounts of water are treated with antifouling agents in order to avoid the growth of algae in the pumping piping.

The high antifouling effectiveness achieved at low dosage, together with the high biodegradability of the compounds according to the invention, can be noted in the low values of the EII (Environmental Impact Index)=1−$EC_{50}$/$LC_1$ (menadione triaminotriazine bisulfite=−1.84; menadione piperazine bisulfite=−2,0), where:

$EC_{50}$ is the concentration that inhibits by 50% the settling of the species of larva used as target;

LC1 is the minimum toxic concentration for the larvae used as target.

The lower the ratio between the two parameters, the less the product pollutes. Otherwise, higher values correspond to a higher likelihood of damaging the ecosystem in which the compound is active.

This index is an empirical value for giving a measurement of the toxicity of the tested components with respect to other organisms and also provides an index of polluting characteristics.

By subtracting this ratio $EC_{50}$/$LC_1$ from 1, the EII has a positive or negative value depending on whether antifouling effectiveness ($EC_{50}$) becomes apparent before or after the minimum toxic concentration ($LC_1$).

Clearly, products having EII values which are positive or in any case negative but close to zero are to be preferred over those which have negative EII values.

The following examples are provided merely as illustration of the present invention and must not be intended as limiting the scope thereof as defined in the appended claims.

EXAMPLE N.1

Comparison Tests Between MBP and MTB

The compounds MBP and MTB were examined in different percentages, singularly and/or in combination, in hard-matrix antifouling formulations containing or not containing copper, as reported in Table I:

TABLE I

| Panel | Formulation | Presence of copper |
|---|---|---|
| P34 | 5% MBP | Yes |
| P35 | 5% MTB | Yes |
| P36 | 5% MBP | No |
| P47 | 5% MTB | No |
| P49 | 3% MBP + 2% MTB | No |

The different paints were applied to the fibreglass panels previously treated with a coating of epoxy paint and then immersed in seawater (dockyard of La Spezia, Italy, 9/5/2000). To determine the deposition or formation of vegetation and micro-organisms, both qualitatively and quantitatively, and to evaluate the antifouling activity of the samples, two different controls were carried out after two months (1^control) and after six months (2^control). The results were shown in Table II:

TABLE II

| Panel | Formulation | Date of immersion | 1^ Control after a two month exposure | 2^ Control after a six month exposure |
|---|---|---|---|---|
| P34 | 5% MBP (+$Cu_2O$) | 09.05.2000 | Removable green, brown-red algae | A few green algae |
| P35 | 5% MTP (+$Cu_2O$) | 09.05.2000 | Removable green, brown-red algae | A few green algae |
| P36 | 5% MBP | 09.05.2000 | Slime, several green, brown-red algae | Several green, brown-red algae |
| P47 | 5% MTB | 09.05.2000 | Slime, several green, brown-red algae | Several green, brown-red algae |
| P49 | 3% MBP + 2% MTB | 09.05.2000 | Slime, several green, brown-red algae | Several green, brown-red algae |

The panels P34 and P35 showed better antifouling properties in particular against algae, serpulidae, acorn barnacles, bryozoas, which were almost absent. These results were achieved through the synergistic action of the derivatives with copper. However, even when they were used alone, the tested products showed a good antifouling activity; in fact, after six months no traces of animal organisms could be observed, but only a limited presence of green, brown-red algae.

EXAMPLE N.2

Comparison Tests Between MBP, MTB, and a Common Commercial Antifouling Compound

The compounds MBP and MTB were examined in different percentages, in hard-matrix antifouling formulations. The tests included the use of a common commercial antifouling product, Ciclor 98, which contains Acyclovir as active ingredient, largely used in the formulation of yatch paints, and a control panel (untreated, without biocide), as it is shown in Table III:

TABLE III

| Panel | Formulation | Presence of copper |
|---|---|---|
| P1 | 3.5% Ciclor 98 | No |
| P2 | 5% Ciclor 98 | No |

TABLE III-continued

| Panel | Formulation | Presence of copper |
|---|---|---|
| P3 | 5% MBP | No |
| P4 | 5% MTB | No |
| P6 | 3.5% MBP | No |
| P7 | 2.0% MBP | No |
| P8 | 3.5% MTP | No |
| P9 | 2.0% MTP | No |
| P10 | Control (Untreated) | No |

The prepared paints were applied to the fibreglass panels previously treated with a coating of epoxy paint and then immersed in seawater (dockyard of Genoa, Italy, 21/7/1999). To determine the deposition or formation of vegetation and micro-organisms, both qualitatively and quantitatively, and to evaluate the antifouling activity of the samples, two different controls were carried out after two months (1^control) and after 4 months (2^control). The results are shown in Table IV:

TABLE IV

| Panel | Formulation | Date of immersion | 1^ Control after a two month exposure | 2^ Controls after a four month exposure |
|---|---|---|---|---|
| P1 | 3.5% Ciclor 98 | 21.7.1999 | Removable green, brown-red algae | Thin film of brown microalgae |
| P2 | 5% Ciclor 98 | 21.7.1999 | Removable green, brown-red algae | Thin film of brown microalgae, a few acorn barnacles |
| P3 | 5% MBP | 21.7.1999 | Removable green, brown-red algae | Clean |
| P4 | 5% MTB | 21.7.1999 | Removable green, brown-red algae | Clean |
| P6 | 3.5% MBP | 21.7.1999 | Removable green, brown-red algae | Thin film of brown microalgae |
| P7 | 2.0% MBP | 21.7.1999 | Removable green, brown-red algae | Thin film of brown micro_algae, bryozoan settlement |
| P8 | 3.5% MTP | 21.7.1999 | Removable green, brown-red algae | Thin film of brown microalgae |
| P9 | 2.0% MTP | 21.7.1999 | Removable green, brown-red algae | Thin film of brown microalgae |
| P10 | Control (Untreated) | 21.7.1999 | Dense settlement of bryozoas, barnacles acorn, polichaetas | Dense settlement of bryozoas, acorn barnacles, polichaetas |

The products MBP and MTB showed an increased antifouling activity, even when compared to the commercial antifouling product Ciclor 98. The control panel P10 displayed hard macrofouling settlement after a four month immersion without biocide.

EXAMPLE N.3

Comparison Tests Between MBP, MTB, MSB and a Common Commercial Antifouling Compound The compounds MBP and MTB were examined in different percentages, in hard-matrix antifouling formulations. The tests included the use of Ciclor 98, the use of menadione sodium bisulphite (MSB) and a control panel (untreated), as is shown in Table V:

TABLE V

| Panel | Formulation | Presence of copper |
|---|---|---|
| P1 | 0.8% MBP (+Cu$_2$O) | Yes |
| P2 | 0.8% MTP (+Cu$_2$O) | Yes |
| P4 | 5% MBP | No |
| P5 | 5% MTB | No |
| P7 | 5% Ciclor 98 | No |
| C | Control (untreated) | No |
| N | 5% MSB | No |

The prepared paints were applied to the fibreglass panels previously treated with a coating of epoxy paint and then immersed in seawater (dockyard of Genoa, Italy, 21/7/1999).

To determine the deposition or formation of vegetation and micro-organisms, both qualitatively and quantitatively, and to evaluate the antifouling activity of the samples, two different controls were carried out after two months (1^control) and after 4 months (2^control). The results are shown in Table VI:

TABLE VI

| Panel | Formulation | Date of immersion | 1^ Control after a two month exposure | 2^ Controls after a four month exposure |
|---|---|---|---|---|
| P1 | 0.8% MBP | 21.7.1999 | Removable green, brown-red algae | Clean |
| P2 | 0.8% MTB | 21.7.1999 | Removable green, brown-red algae | Clean |
| P4 | 5% MBP | 21.7.1999 | Removable green, brown-red algae | A few acorn barnacles |
| P5 | 5% MTB | 21.7.1999 | Removable green, brown-red algae | A few acorn barnacles |
| P7 | 5% Ciclor 98 | 21.7.1999 | Removable green, brown-red algae | Several acorn barnacles |
| C | Control (untreated) | 21.7.1999 | Dense settlement of bryozoas, acorn barnacles, polichaetas | Dense settlement of bryozoas, acorn barnacles, polichaetas |
| N | 5% MSB | 21.7.1999 | Dense settlement of bryozoas, acorn barnacles, polichaetas | Dense settlement of bryozoas, acorn barnacles, polichaetas |

The panels P1, P2 and P8 showed excellent antifouling effectiveness achieved through the synergistic action of the MBP and MTB derivatives in association with Cu$_2$O.

Moreover, MBP and MTB not associated with Cu$_2$O (P4 and P5 panels) also showed an excellent antifouling activity, more than Ciclor 98 (panel P7). On the contrary, the menadione sodium bisulphite (MSB) did not show any antifouling activity (panel N).

What is claimed is:

1. A method for inhibiting the growth and deposition of a layer of algae, mold or microorganisms on a substrate in need of treatment, comprising applying an antivegetative, biocidal effective amount of a compound selected from the group consisting of menadione triaminotriazine bisulfite(I) (MTB) and menadione(bis) piperazine bisulfite(II) (MBP) to a substrate.

2. The method according to claim 1, wherein said compound is in association with a carrier useful for the application to a substrate in contact with water.

3. The method according to claim 1, wherein said compound has a concentration of 0.5% to 10% by weight.

4. The method according to claim 1, wherein said substrate comprises fishing net.

5. A method for inhibiting the growth and deposition of a layer of algae, mold or microorganisms in a substrate in need of treatment, comprising applying an antivegetative, biocidal effective amount of a compound selected from the group consisting of menadione triaminotriazine bisulfite(I) (MTB) and menadione(bis) piperazine bisulfite(II) (MPB) to said substrate, wherein said substrate comprises cooling water of industrial plants.

6. An antifouling composition consisting essentially of a compound selected from the group consisting of menadione triaminotriazine bisulfite (I) (MTB) and menadione(bis) piperazine bisulfite (II) (MBP) in association with a carrier.

7. An antifouling paint comprising an antivegetative, biocidal effective amount of a compound selected from the group consisting of menadione triaminotriazine bisulfite(I) (MTB) and menadione(bis) piperazine bisulfite (II) (MBP) dispersed in a paint carrier.

* * * * *